United States Patent
Benja-Athon

Patent Number: 5,861,015
Date of Patent: *Jan. 19, 1999

[54] MODULATION OF THE NERVOUS SYSTEM FOR TREATMENT OF PAIN AND RELATED DISORDERS

[76] Inventor: Anuthep Benja-Athon, 210 E. 36th St., Ground Floor, New York, N.Y. 10016

[*] Notice: This patent issued on a continued prosecution application filed under 37 CFR 1.53(d), and is subject to the twenty year patent term provisions of 35 U.S.C. 154(a)(2).

[21] Appl. No.: 851,181

[22] Filed: May 5, 1997

[51] Int. Cl.$^6$ ........................................... A61N 1/04
[52] U.S. Cl. .............................................. 607/46; 128/907
[58] Field of Search ................................. 607/46; 128/907

[56] References Cited

U.S. PATENT DOCUMENTS

| | | | |
|---|---|---|---|
| 4,989,604 | 2/1991 | Fang | 128/907 |
| 4,989,605 | 2/1991 | Rossen | 607/46 |
| 5,094,242 | 3/1992 | Gleason et al. | 128/907 |
| 5,425,752 | 6/1995 | Vu'Nguyen | 128/907 |
| 5,449,378 | 9/1995 | Schouenborg | 607/46 |

*Primary Examiner*—William E. Kamm
*Assistant Examiner*—Carl H. Layno

[57] ABSTRACT

The medical method of treating pain and inflammations including neurogenic inflammation of the visceral or somatic organ known herein as the effector in human body involve and mediate by the afferent nervous system and the autonomic nervous system innervating the visceral or somatic organ. The method is the application of an electrical current stimulus or an electromagnetic stimulus to aforementioned nervous systems innervating adjacent or distant soft tissues known herein as the affector. The technique is the reversibly and percutaneously implanting a pair of anode needle electrode and cathode needle electrode or a concentric needle electrode functioning with an anode and a cathode in the affector and passing of electrical current of sufficient amperage to excite or inhibit the activity of the nerves and the nerve receptors innervating the affector. Electrical current is transmitted from a current generating device through the electrical leads to the electrode(s) and then to the nerves and the nerve receptors. Alternative stimulus is the transcutaneous electromagnetic stimulus delivered to the nerves and the nerve receptors by the application of the transcutaneous electromagnetic stimulus producing device over the nerves and the nerve receptors innervating the affector.

14 Claims, 1 Drawing Sheet

MODULATION OF THE NERVOUS SYSTEM FOR TREATMENT OF PAIN AND RELATED DISORDERS

FIELD OF INVENTION

Method of stimulating the afferent and autonomic nervous systems in a soft tissue structure in the treatment of pain and inflammations.

BACKGROUND OF THE INVENTION

The objective of the present invention is a medical method of effective management and treatment of many forms of acute and chronic pain, inflammations including neurogenic inflammation and related disorders of visceral and somatic organs in human and other animal species.

Pain, inflammations and related disorders are universal experience of every human. Pain is the most common symptom and the most frequent cause of suffering and disability. The tangible cost to the society is in hundreds of billions of dollar per annum in treatment and loss of wage and productivity. In this century much knowledge on pain and related disorders is acquired but still little is known. The famous Melzack and Wall's Theory of Gate Control gives some insight into pain modulation. Worse, the proper treatment is even less known.

Many of the pain and inflammation conditions including neurogenic inflammation and related disorders of visceral and somatic organs involve, are mediated and perpetuated by the afferent nervous system and autonomic nervous system are responsive to treatment method of the present invention. It will be discovered that many of the pain and inflammations and related disorders of the visceral and cardiovascular organs which elude scientific explanation and treatment will follow the scheme of the present invention.

To understand the preferred embodiments of the present invention, it is necessary to introduce the present applicant's Innervation Unit© which is defined as: Any parts and organs in an Innervation Unit having same, related, linked, connected, coupled anatomy, neuroanatomy and neurophysiology by and in either the peripheral nervous system, central nervous system, or both.

The present invention is the therapeutic technique of treating many forms of acute and chronic pain and inflammations including neurogenic inflammation. Many of said pain and inflammations either are recalcitrant to standard medical treatments or totally failed to respond to the standard medical and surgical treatments causing morbidity, disability and even death in patient. Many of said pain and inflammations involve and mediate by the afferent of the sensory nervous system and the afferent of the autonomic nervous system and, subsequently, involved the efferent nervous system of the autonomic nervous system and the motor nervous system. Two of the many common disorders which can be very recalcitrant to standard medical treatments or totally failed to respond to the standard medical and surgical treatments causing morbidity and disability in patients cited herein as examples which have been successfully treated with the process described herein are the reflex sympathetic dystrophy of the upper extremity and repetitive strain injuries and cumulative traumatic disorders of the head, neck, shoulders, thorax, lower back, upper and lower extremities.

To perform the therapeutic process of the present invention in human, it is necessary to understand this applicant's scientific concept supporting the claims of the present invention. Many of said pain and inflammations involve and are mediated and perpetuated by the afferents of the sensory nervous system and the autonomic nervous system which innervate said disordered visceral or somatic organs known herein as the effector. Said effector is such as, but not limited to, painful and inflamed the large intestine, arthropathies, neuropathies, neuralgia, neuropathic pain, neurogenic pain, reflex sympathetic dystrophy, postsurgical pain, posttraumatic pain, chronic musculoskeletal pain including aforementioned anatomical parts, weakness and dysfunction. On the other hand, the soft tissues such as, but not limited to, retinaculum, ligament, tenosynovium, synovium, tendon, tendomuscular, intrafusal fibers, periosteum, known herein as the affector is also concurrently innervate by said afferents of said sensory nervous system and autonomic nervous system. Said effector and said affector are defined to be in the same Innervation Unit wherein both are neuroanatomically and neurophysiologically linked, related, connected, coupled in the peripheral nervous system and/or central nervous system at the spinal cord and/or at the brain level such as in the gray matter and the ascending and descending tracts of the spinal cord, midbrain such as the thalamus, and forebrain. In addition, said individual affector and effector may be anatomically adjacent to each other or are anatomically far apart. For example—1) the flexor retinaculums of the forearm and wrist being the affector and the effector is the painful and inflamed ipsilateral digital joints and ipsilateral wrist joints, such as, but not limited to the carpocarpal joints involve in the famous carpal tunnel syndrome; 2) intrafusal fibers of the trapezius muscle being the affector and the effector is the cervical joints, cervical soft tissues, and frontal headpain.

SUMMARY OF THE INVENTION

Pain and inflammations are universal daily experience of every human. In this century much knowledge on pain, inflammations and related disorders is acquired but still little is known. Worse, the proper treatment is even less known.

The objective of the present invention is an expeditious, effective, yet simple treatment of aforementioned disorders to reduce morbidity and mortality.

Essentially, the medical method of the present invention arose from the knowledge that the afferent and autonomic nerves innervating and nerves' receptors in the soft tissues such as, but not limited to, retinaculum, ligament, tenosynovium, synovium, tendon, tendomuscular, intrafusal fibers, periosteum known herein as the affector and the afferent and autonomic nerves innervating painful and inflamed visceral or somatic organ, known herein as the effector, are neuroanatomically and neurophysiologically related in peripheral nervous system and in the central nervous system and that these afferent and autonomic nerves are involved and mediate pain, inflammations including neurogenic inflammation and related disorders. By exciting or inhibiting the nerves and nerve receptors innervating an affector which may be adjacently or distantly located from the effector, the result is the attenuation or elimination of pain and inflammations of the afflicted effector having the same afferent neuronal circuitry and autonomic neuronal circuitry as that of the affector.

The medical method is the reversibly and percutaneously implanting a concentric needle electrode with anode and cathode, or one anode electrode and one cathode electrode in the affector to excite or inhibit the activity of the nerves and nerve receptors innervating the affector. Electrical current is passed from a current generating device to the electrode to the nerves and nerve receptors. Alternative stimulus is the transcutaneous electromagnetic stimulus to said nerves.

PREFERRED EMBODIMENTS OF THE INVENTION

Figure 1:
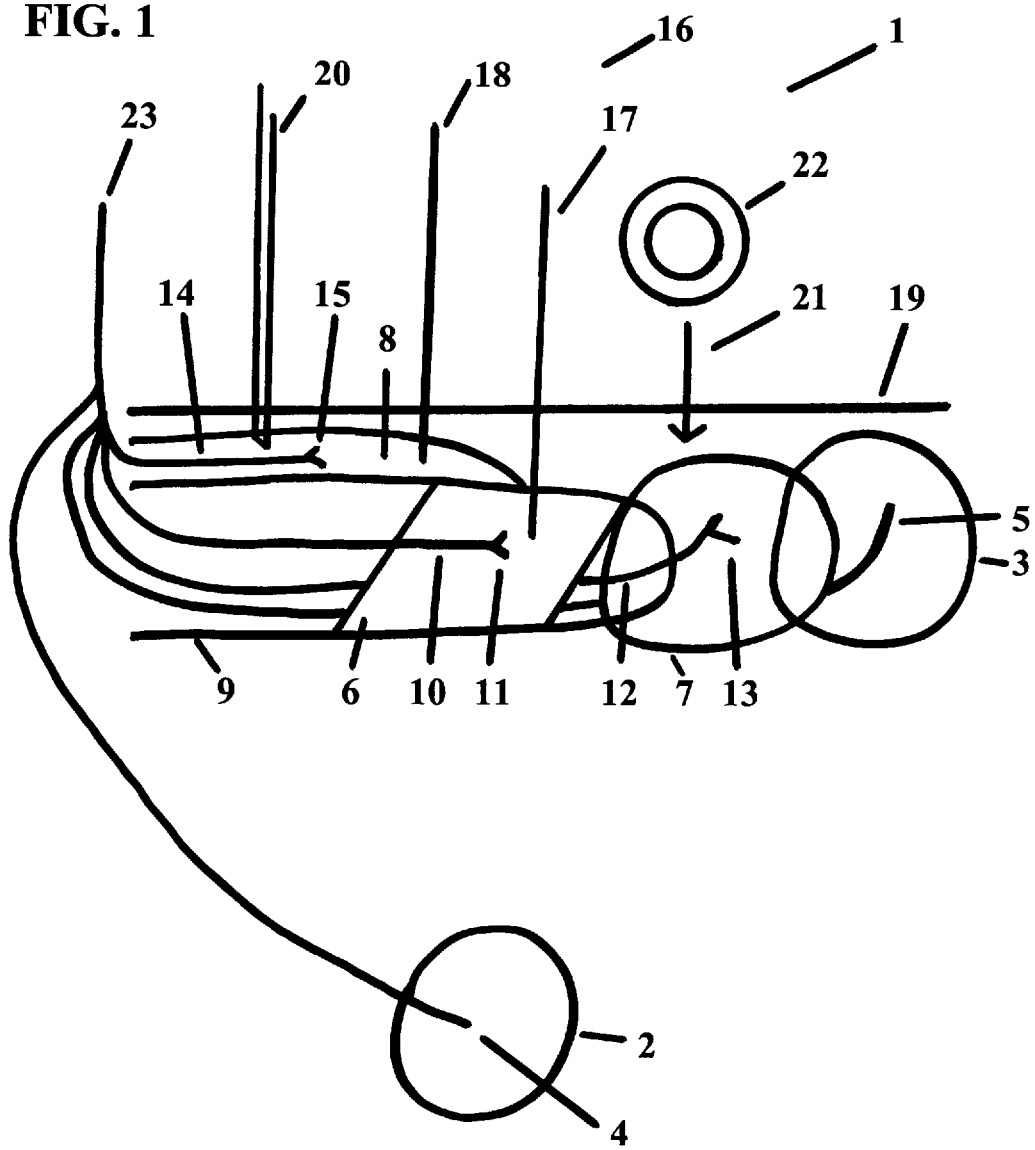
FIG. 1 shows the schematic of the present invention.

FIG. 1 shows the therapeutic process 1 of the present invention for treating pain and inflammations including neurogenic inflammation of the visceral organs 2 and somatic organs 3 known herein as the effector in the human body or in an animal wherein said pain and inflammations of visceral organs 2 involve and are mediated by the nerves 4 of the afferent nervous system and the autonomic nervous system innervating visceral organs 2 and wherein said pain and inflammations of somatic organs 3 involve and are mediated by the nerves 5 of the afferent nervous system and the autonomic nervous system innervating somatic organs 3.

Therapeutic process 1 comprises the application of a stimulus means 16 to the nerves of said afferent nervous system and autonomic nervous systems concurrently innervating the soft tissue such as, but not limited to, the retinaculum 6, ligament 7, tenosynovium, synovium, tendon, tendomuscular, intrafusal fibers collectively shown as 8 and periosteum 9. Said soft tissue is known herein as the affector in the same Innervation Unit as said effector. Said innervation is, but not limited to, nerve 10 and nerve receptors 11 innervate retinaculum 6, nerve 12 and nerve receptors 13 innervate ligament 7, nerve 14 and nerve receptors 15 innervate tenosynovium, synovium, tendon, tendomuscular, intrafusal fibers 8.

Base on the aforementioned concept, a physician knowledgeable in anatomy, neurology, neuroanatomy and neurophysiology will be able to choose the neuroanatomically and neurophysiologically relevant affector and the anatomical location of said affector such as, but not limited to, the retinaculum 6 in the wrist, the iliolumbar ligament 7 in the low back, tenosynovium 8 of a muscle, synovium 8 of a joint, tendon 8 of a muscle, tendomuscular 8 of a muscle, intrafusal fibers 8 of a muscle, or periosteum 9 of bone to be used as an affector for treating said pain, inflammations and related disorders affecting the corresponding neuroanatomically and neurophysiologically relevant visceral organs 2 and somatic organs 3.

After an affector was chosen as discussed supra, routine surgical technique is followed for the application of stimulus means 16. The therapeutic technique comprises:

1) The use of an anode needle electrode 17 and a cathode needle electrode 18 which are reversibly and percutaneously inserted through the skin 19 of a patient and implanted so that the tip and adjacent portion of the shaft of said electrode are in the affector. In FIG. 1, electrodes 17 is in retinaculum 6 and is in contact with or adjacent to said nerves 10 and nerve receptors 11. FIG. 1 further shows that both electrodes 17 and 18 do not have to be in the same type of organ system; in other words, for example, electrode 17 is in retinaculum 6 and electrode 18 is in adjacent ligament 7. Obviously, when said two monopolar electrodes 17 and 18 are used and implanted in said affector, both electrodes are separated by a small distance depending on the size of the affector so that there is no interruption of the flow of electrical current. Standard and readily available monopolar acupuncture pin and needle are used with range of lengths of about 20–125 millimeters and a range of cross-sectional diameters of 0.1 mm–0.71 mm. The excitation and inhibition of said nerves and nerve receptors are achieved by passing 1–500 hertz direct electrical current from a common commercially available current generating device via electrical leads to said electrodes 17 and 18 to said nerves and nerve receptors innervating said effector. The application of said current stimulus is approximately for 1 minute–15 minutes although said time may vary depending on several physical and biological factors such as applied voltage and amperage, resistance, placement of said electrodes relative to said nerves and nerve receptors. Patient should be able to perceive said action potential generation by the sensation perceived. The disposable electrode is reversibly removed from said affector and body and discarded after the application. All electrodes are sterile and single-use disposable.

2) The use of a concentric metallic needle electrode 20 which is reversibly and percutaneously inserted through skin 19 of a patient so that the tip and adjacent portion of the shaft of electrode 20 are in either tenosynovium, synovium, tendon, tendomuscular, or intrafusal fibers 8 as shown in FIG. 1. Other affector such as, but not limited to, retinaculum 6, ligament 7, or periosteum 9 can be used in place of said affector. In FIG. 1, electrode 20 is in tenosynovium, synovium, tendon, tendomuscular, or intrafusal fibers 8 and is in contact or adjacent to nerves 14 and nerve receptors 15 innervating said affector. Concentric metallic needle electrode 20 has a range of lengths of 25–125 millimeters and a range of cross-sectional diameters of 0.1 mm–0.71 mm and has an anode and a cathode for the flow of electrical current. Electrode 20 supplies a 1–500 hertz direct electrical current stimulus in a range of microampere to milliampere to nerves 14 and nerve receptors 15 innervating said affector. Said excitation and inhibition is achieved by passing 1–500 hertz direct electrical current from a common commercially available current generating device via electrical leads to electrode 20 to nerves 14 and nerve receptors 15 innervating said affector. The application of said current stimulus is approximately for 1 minute–15 minutes although said time may vary depending on several physical and biological factors such as applied voltage and amperage, resistance, placement of electrode 20 relative to said nerves and nerve receptors. Patient should be able to perceive said action potential generation by the sensation perceived. The disposable electrode is reversibly removed from said affector and body and discarded after the application. The electrode is sterile and single-use disposable.

3) The application of the transcutaneous electromagnetic stimulus 21 to afferent nerves 12 and nerve receptors 13 innervating said affector such as, but not limited to, ligament 7 as shown in FIG. 1. Afferent nerves and nerve receptors innervating retinaculum 6, tenosynovium, synovium, tendon, tendomuscular, intrafusal fibers collectively shown as 8, periosteum 9 can be similarly used for stimulation. The transcutaneous electromagnetic stimulus 21 is produced by a common commercially available transcutaneous electromagnetic stimulus producing device 22. Device 22 delivers stimulus 21 to nerves 12 and nerve receptors 13 innervating said affector as per routine standard application of commercially available transcutaneous electromagnetic stimulus producing device. The transcutaneous electromagnetic stimulus strength within the generated electromagnetic field is sufficient to cause excitation or inhibition of the activity of said nerves 12 and nerve receptors 13. Said electromagnetic stimulus strength in said field depends on several physical and biological factors such as the placement of the transcutaneous electromagnetic stimulus device over the skin, skin and deep tissue resistances, location of said nerves and nerve receptors.

The result of said therapeutic method is the modulation 23 in the peripheral nervous system and/or central nervous system at the spinal cord and/or at the brain level of the afferent nervous system, the autonomic nervous system and the efferent nervous system innervating said effector-visceral organs 2 and somatic organs 3.

Although various preferred embodiments of this invention have been described, it will be appreciated by those skilled in the art that variations and adaptations may be made without departing from the spirit of the invention or the scope of the aforementioned claims.

Although the preferred techniques, stimuli, and instruments have been described in this application, it will be appreciated by those skilled in the art variations and adaptations may be made to said modes without departing from the spirit of the invention or the scope of the aforementioned claims.

Although various preferred embodiments of this invention have been described in human, it will be appreciated by those skilled in the art that its application and use can be applied in other living species without departing from the spirit of the invention or the scope of the claims.

I claim:

1. Medical method of treating pain and inflammations including neurogenic inflammation of the visceral and somatic organs wherein said pain and inflammations involve and are mediated by the nerves of the afferent nervous system and the autonomic nervous system innervating said visceral organ and somatic organ known herein as the effector in the human body or in an animal by the application of a stimulus means to said nerves and the nerve receptors of said systems concurrently innervating the soft tissue which is retinaculum, ligament, tenosynovium, synovium, tendon, tendomuscular, intrafusal fibers, periosteum known herein as the affector of said body comprises the process of generating and inhibiting action potential of said nerves and nerve receptors innervating said affector.

2. The medical method according to claim 1 wherein the process of generating and inhibiting action potential of said nerves and nerve receptors comprises the application of a stimulus means which is a direct electrical current having a frequency 1–500 Hertz to said nerve and nerve receptors.

3. The medical method according to claim 1 wherein the process of generating and inhibiting action potential of said nerves and nerve receptors comprises the application of a stimulus means which is a transcutaneous electromagnetic stimulus to said nerve and nerve receptors.

4. The medical method according to claim 1 wherein said process of generating and inhibiting action potential of said nerves and nerve receptors innervating said affector is the application of a 1–500 hertz direct electrical current stimulus in a range of microampere to milliampere via said needle electrode means to said nerves and nerve receptors.

5. The medical method according to claim 1 wherein said process of generating and inhibiting action potential of said nerves and nerve receptors innervating said affector involves application of transcutaneous electromagnetic stimulus to said nerves and nerve receptors.

6. The medical method according to claim 1 wherein said process of generating and inhibiting action potential of said nerves and nerve receptors innervating includes said process reversibly and percutaneously implanting a concentric metallic needle electrode in contact or adjacent to said nerves and nerve receptors.

7. The medical method according to claim 1 wherein said process of generating and inhibiting action potential of said nerves and nerve receptors innervating said affector includes reversibly and percutaneously implanting one anode electrode and one cathode electrode which are separated by a small distance in direct contact or adjacent to said nerves and nerve receptors.

8. The medical method according to claim 1 wherein said process of generating and inhibiting action potential of said nerves and nerve receptors innervating said affector includes application of transcutaneous electromagnetic stimulus in tesla unit to said nerves and nerve receptors.

9. The medical method of treating pain and inflammations including neurogenic inflammation of the visceral and somatic organs wherein said pain and inflammations involve and are mediated by the nerves of the afferent nervous system and the autonomic nervous system innervating said visceral organ and somatic organ known herein as the effector in the human body or in an animal by the application of a stimulus means to said nerves and the nerve receptors of said systems concurrently innervating the soft tissue which is retinaculum, ligament, tenosynovium, synovium, tendon, tendomuscular, intrafusal fibers, periosteum known herein as the affector of said body wherein the process of generating and inhibiting action potential of said nerves and nerve receptors comprises:

the process of reversibly and percutaneously implanting electricity conducting needle electrode means into said affector; and the process of application of transcutaneous electromagnetic stimulus to said nerves and nerve receptors.

10. The medical method according to claim 9 wherein said process of reversibly and percutaneously implanting electricity conducting needle electrode means into said affector is the percutaneous insertion of needle electrode means into said affector wherein said needle electrode means is in contact or adjacent to said nerves and nerve receptors innervating said affector.

11. The percutaneous insertion of needle electrode means in claim 10 includes inserting a concentric metallic needle electrode which has a range of lengths of 25–125 millimeters, a range of cross-sectional diameters of 0.1 mm–0.71 mm., and an anode and a cathode for the flow of said electrical current stimulus to said nerves and nerve receptors innervating said affector.

12. The percutaneous insertion of needle electrode means in claim 10 includes inserting one anode needle electrode and one cathode needle electrode for the flow of said electrical current stimulus to said nerves and nerve receptors innervating said affector.

13. The process according to claim 9 is the reversibly and percutaneously implanting said anode needle electrode and said cathode needle electrode separated by a distance into said affector wherein said electrodes are in contact or adjacent to said nerves and nerve receptors innervating said affector.

14. The implanting steps in claim 13 wherein the step of implanting needle electrodes comprises implanting metallic needle electrodes which have a range of 20–125 millimeters and a range of cross-sectional diameters of 0.1 mm–0.71 mm.

* * * * *